United States Patent [19]

Greten et al.

[11] Patent Number: 5,042,341
[45] Date of Patent: * Aug. 27, 1991

[54] MARKING STATION FOR TIMBER

[75] Inventors: Ernst Greten, Delligsen; Klaus Jurisch, Hattstedtermars, both of Fed. Rep. of Germany

[73] Assignee: Fagus-GreCon Greten GmbH & Co. KG, Leine, Fed. Rep. of Germany

[*] Notice: The portion of the term of this patent subsequent to Jun. 19, 2007 has been disclaimed.

[21] Appl. No.: 485,440

[22] Filed: Feb. 27, 1990

[30] Foreign Application Priority Data

Mar. 11, 1988 [DE] Fed. Rep. of Germany ....... 3808119

[51] Int. Cl.$^5$ ............................................. B27L 5/08
[52] U.S. Cl. ..................................... 83/75.5; 83/76.8; 83/365; 83/368; 83/371
[58] Field of Search ................. 83/75.5, 371, 365, 363, 83/368, 76.8; 356/429, 430, 431

[56] References Cited

U.S. PATENT DOCUMENTS 4,914,269 4/1990 Kinsman et al. ............... 214/121.64
4,934,229 6/1990 Greten et al. ...................... 83/371 X Primary Examiner—Paul A. Bell
Assistant Examiner—Kenneth E. Peterson
Attorney, Agent, or Firm—Michael J. Striker

[57] ABSTRACT

A marking station for defect locations and quality limits in timber includes a timber transporting device, a transporting speed changing device, and an indicating station part with a laser transmitting element formed as a mirror, and laser. The laser is arranged stationary so that the laser beam extends parallel to a movement direction of the timber and impinges on the mirror. The mirror deviates the laser beam transversely to the movement direction. The laser beam indicates on the timber, in the movement direction, a first separating plane before a defect location and a second separating plane behind the defect location. The laser beam also indicates quality limits. Indicating positions of the laser transmitting element are transmitted to a computer.

12 Claims, 14 Drawing Sheets

MARKING STATION FOR TIMBER

CROSS-REFERENCE TO RELATED APPLICATION

This application is a continuation-in-part of U.S. patent application Ser. No. 322,076 filed on Mar. 10, 1989, and entitled "Marking Station for Timber", now U.S. Pat. No. 4,934,229.

BACKGROUND OF THE INVENTION

The present invention relates to a marking station for timber. More particularly, it relates to such a marking station which is used for defect locations and quality limits in timber and provided with a transporting device, a device for changing a transporting speed of the timber, and an indicating station part with a laser transmitter element for indicating first and second separating planes before and after a defect location and quality limits with a laser beam. The laser transmitter element can be moved by an operator along a guiding device parallel to the movement direction to indicating positions corresponding to the separating plane and the quality limits, and the indicating positions of the laser transmitter element are supplied to a computer for controlling in some cases an optimizing saw.

Marking stations of the above mentioned general type are known in the art. One of such marking stations is operative for stopping the timber upon recognition of a location to be indicated. It has been shown on Hannover Fair Ligna 1987 between May 27, 1987, and June 2, 1987, by the company Wadkin Leicester, Green Lane Works, Leicester LE5 4PF, England. The laser transmitter element is here the laser itself, and it is moved by the operator along the timber with a rope system to the respective indicating position. Because of the high mass of the laser transmitter element, it is quite difficult and relatively slow. Also, the constant holding of the timber for indicating makes the operation longer in an undesirable manner.

Another marking station is disclosed in the German document DE-GM 8,704,684.9. Here a laser 4 is arranged above the timber 3 and the operator 10 is located laterally of the timber. The laser sends a flat beam fan 9 perpendicularly to the transporting direction 11. The beam fan 9 shows on the timber 3 the separating plane with a light band 7 directly on the upper and front side and is reflected onto the lower and rear side through an inspection mirror 5. The inspection mirror 5 is arranged in an inclined manner near and under the timber 3 relative to the horizontal plane so that its normal 6 is directed toward the laser 4. The timber 3 is brought by the operator through a system of light barriers 19 and 21 to a standstill and then displaced manually to the respective indicating position. There an indicating signal is produced and supplied to a computer which is activated by measuring wheels 12, 16 and controls for example a cross-cut saw. The structural expenses are very high. The positioning of the timber 3 manually is time consuming. There is the danger that the eyes 10 of the operator can be hit by the laser beam 9 reflected from the inspection mirror 5.

A further marking station is disclosed in the German reference DE-OS 2,807,670. Here the timber 2 is transported transversely through an inspection zone 10. A stationary laser 26 sends a laser fan 27 onto a mirror 23 which is turnable above the inspection zone 10 about an axis 24 extending parallel to the movement direction of the timber 2. Through a follow-up control 22 the mirror 23 follows the turning of a handle 18 on an operator chair 13. The whole inspection zone 10 including the timber 2 located in it, is run over with the reflected laser fan 27 by actuation of the handle 18. A laser band 29 shows a separating plane whose position is introduced via a pushbutton 33 on the handle 18 as signal through a conductor 32 into the electronic circuit 31. The structural expenses here are also very high. The accuracy of the position detection is low because of the high turning ratio of the laser fan 27 because of the non-constant and great distance of the operator from the individual longitudinal regions of the timber 2.

The German document DE-OS 3,116,253 discloses a measuring system for example for a vehicle 1. A measuring bar 8, 21, 25 extends laterally parallel to the longitudinal axis of the vehicle 1, and a laser 10, 28, 30 is stationarily arranged on its one end. The laser sends a bundled laser beam parallel to the measuring bar. A part of the laser beam is deviated perpendicularly through a first deviating unit 12, 26, 34 in the direction of the vehicle 1. The remaining portion of the laser beam passes through the first deviating unit. This remaining portion can be deviated by a stationary second deviating unit 13 on the other end of the measuring bar 8 about 90° along a further measuring bar 9, and there deviated by a third deviating unit 14 again by 90° in direction of the vehicle 1 as shown in FIG. 1. The remaining portion of the laser beam can also be deviated in a fourth deviating unit 27, 35 on the first measuring bar 21, 25 in direction of the vehicle 1 as shown in FIGS. 2 and 3. The deviating units with the exception of the stationary second unit 13, are displaceable by the operator 15 manually or by a motor along their measuring bars and have a detector 40, 41 for markings 42 on the measuring bar. The detector detects the actual value of each measuring position of its deviating unit and performs the comparison with a nominal value for the associated measuring point 2-7 of the vehicle 1.

The German reference DE-OS 2,654,872 discloses a system of searching and optimizing for example for timber. A stationary laser 30 sends a laser beam in a beam separator 32, and its both output beams are deviated on surfaces of a rotatable polygonal mirror 34 and then on several mirrors 36, 38 and 40, 42, 44. Each output beam scans finally a surface of the timber 10 over an angle 46, 48 in a reciprocating manner. Two photodetectors 50, 52 and 54, 56 are directed to each surface and supply the sensing signals in an electronic evaluating circuit for automatically recognizing defect locations in the timber. This system requires high structural and circuitry expenses.

The German reference DE-PS 3,208,042 shows a system for testing of running material, especially a paper web 18, as to non-directional longitudinal and transverse defects 13 and 14. Here a laser beam from a stationary laser 1 is extended, subdivided and stretched until parallel partial beams 23 strike on a fast rotating polygonal mirror 8. The partial beams 23 are reflected on the material web 18 and form on it flying light points along the transversely extending testing line 27. The beams 24 reflected from the material web are received by a photoelectric converter 16 and converted into signals which are evaluated in an evaluating stage 17.

SUMMARY OF THE INVENTION

Accordingly, it is an object of the present invention to provide a marking station for defect locations and quality limits in timber, which avoids the disadvantages of the prior art.

More particularly, it is an object of the present invention to provide a marking station for defect locations and quality limits in timber, which has an increased output than the known marking stations and provides for an easy and reliable operation by an operator.

In keeping with these objects and with others which will become apparent hereinafter, one feature of the present invention resides, briefly stated, in a marking station of the above mentioned general type in which a laser transmitter element is formed as a first mirror, a laser is arranged stationarily, a laser beam of the laser extends parallel to a movement direction of the timber and impinges on the first mirror, the first mirror deviates the laser beam transversely to the movement direction in a plane as a laser fan, and a first part of the laser fan impinges directly on a first side surface of the timber facing toward the first mirror and also on an upper surface of the timber and indicates there the respective separating plane and quality limit.

Because of the stationary arrangement of the laser and the formation of the laser transmitter element as a mirror, the laser transmitter element becomes very light. The mirror can be moved easily and fast by the operator to the desired indicating position. The mirror becomes so movable that normally the indication can be provided during the further movement of the timber. Only in exceptional cases the operator brakes the timber for indication to a full stop. As long as the optimal indication is achieved, the associated position data is transmitted by the operator to the computer. The laser can send a fanned laser beam which is then deviated by the mirror and further fanned. For this purpose, the mirror is formed flat. Advantageously, the mirror deviates the laser beam perpendicularly to the movement direction. By forming the laser transmitting element as a light transmitter and providing a flexible optical waveguide for connecting a stationary laser with the light transmitter which transmits a laser fan transversely to the transporting direction, even more lower structural expenses are achieved with simultaneous increase in the operating reliability of the marking station.

In accordance with another feature of the present invention, a flat inspection mirror extends stationarily under the timber in the movement direction, and a second part of the laser fan is reflected by the inspection mirror to a lower surface of the timber and indicates there the associated separating plane and quality limit. With these features, an indication on the lower surface of the timber as well is achieved by simple means. For adjusting to the stature and/or the standing position of the operator, the inspection mirror can be adjusted as to its inclination relative to the horizontal plane about an axis which extends parallel to the movement direction. The operator observes the indication on the lower surface of the timber in the inspection mirror.

Quality limits of an individual timber are indicated by the operator also with the laser fan and with their position data are transmitted to the computer. The computer determines on the base of its programming whether the optimizing saw must or must not deliver a saw cut on the quality limit. In contrast to this, a defect location in the timber controls the optimizing saw in each case so that it performs a sawing cut both in the first separating plane as well as in the second separating plane to eliminate the defect location from the timber. In the latter case, with skilled handling of the first mirror by the operator, both the first and subsequently the second separating planes are indicated with the same first mirror and the positions are transferred to the computer. These indicators and transmittals of both separating planes which follow one another in a short time can take place in further moving timber, while the operator can reduce the output transporting speed of the timber when needed.

In accordance with a further feature of the present invention, the first mirror indicates the first separating plane on the timber, while a further laser transmitter element formed as a second mirror is moved along the guiding means and parallel to the movement direction by the operator for indicating the second separating plane on the timber by means of a laser fan in the respective indicating position relative to the timber. The first mirror can be made partially permeable so that a part of the laser beam falls through the first mirror on the second mirror. When the laser is arranged on the other side of the mirror, the laser beam falls naturally first on the second mirror, which in the case can be made partially permeable, and a part of the laser beam passes to the first mirror.

Still another feature of the present invention is that each of the mirrors is mounted on a carriage which is guided by the guiding device. These features enable an especially exact and easy guidance of the carriages.

With the use of two mirrors, one of the carriages can be provided with a hand switch, and the hand switch can control the distance between both carriages and thereby both separating planes. In this manner the distance between both mirrors are adjusted relative to one another in a simple and fast manner. The carriage of the second mirror can be provided for example with a drive which is controlled by the hand switch on the other carriage.

The transporting speed of the transporting device can be controlled in dependence upon the position of the mirror along the guiding device so that the transporting speed is maximal when the mirror is located in an inlet region of the marking station, and is minimal when the mirror is located in the outlet region of the marking station. These features prevent a situation that the timber leaves the marking station too fast, for example before the completion of the indication and then must be returned to the marking station. Advantageously, the transporting speed changes linearly between its extreme values.

The controlled transporting speed can be selectively superposed by a basic transporting speed of a constant value by actuation of a foot switch. This provides for a further possibility for influencing the transporting speed of the timber in the marking station.

Each mirror can be provided with a first displacement transmitter which produces first output signals corresponding to the position of the associated mirror, and the transporting device can be provided with a second displacement transmitter which produces second output signals corresponding to the position of the timber along the transporting device, the first and second output signals being entered into the computer. In this way the output signals can be produced in a simple and cost-favorable manner and made available for the computer.

The indication station portion can be followed by a marking device of the marking station and the marking device can be controlled by the computer so that the separating planes and quality limits indicated in the indicating station portion remain marked on the timber. With these features, when needed a remaining marking of the previously made laser indications can be achieved. This can be used for control of the operator when it is feared that the operator performs the laser indicator on the timber not sufficiently thoroughly. The marking device can be formed for example as an ink spraying printer.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 18 is a partial perspective view of yet another embodiment of a marking station according to the invention.

DESCRIPTION OF THE PREFERRED EMBODIMENTS

Figure 1:
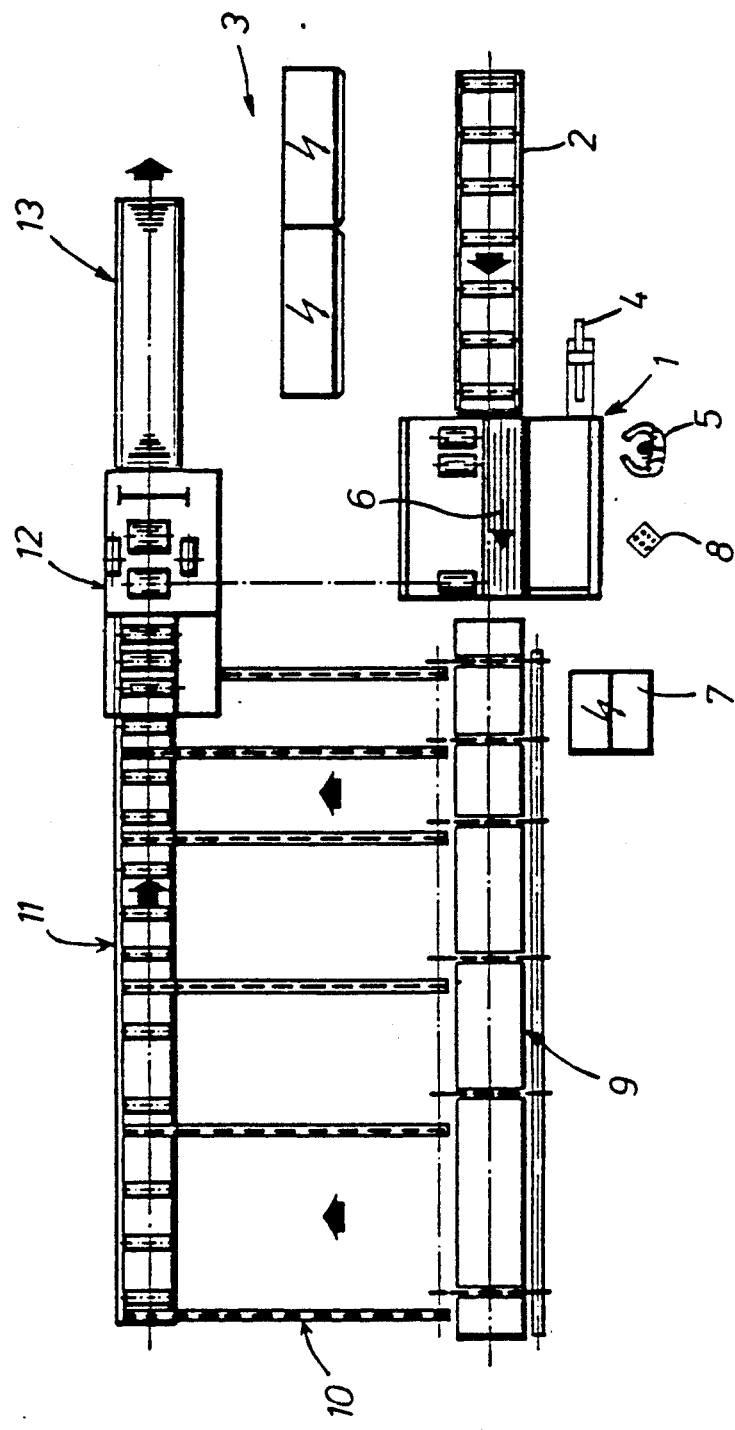
FIG. 1 is a schematic plan view of a marking station in accordance with the present invention with installation parts located before and after the same.

A marking station 1 in accordance with the present invention is shown in FIG. 1 as a part of an installation to which timber is supplied one after the other in the direction of the arrow by a roller conveyor 2. The timber can also be final products which do not allow any remaining marking. The installation includes a cutting device 3 for processing timber of up to nine qualities. An optimization of the timber use with consideration of different qualities and prices for reaching an economical solution must be provided.

A timber can have for example several quality stages. The transition between neighboring quality stages is indicated in the marking station 1 with a laser beam supplied by a stationary laser 4. Similarly, separating planes before and after a location of defect in the timber can be indicated with the laser beam. This indication is performed in that an operator 5 deviates the laser beam which extends from the laser 4 parallel to a movement direction 6 of the timber in the marking station 1, the deviation is carried by a mirror which is not shown in FIG. 1 and advantageously perpendicularly to the movement direction 6 in direction of the timber. The indications can be obtained during the running timber or also in its rest position.

Each indication of a quality limit or a separating plane next to a location of defect is introduced by the operator 5 into a computer 7 by pressing a key on a hand switch which is not shown in FIG. 1. In the same manner the operator 5 introduces different qualities of the timber into the computer 7 by a keyboard 8.

When the thus registered timber leaves the marking station 1 in the movement direction 6, it arrives at a buffer zone 9 and from there via a transverse conveyor 10 in a transverse direction to a roller conveyor 11. The roller conveyor 11 transports the timber in the direction of arrow to an optimizing saw 12. The latter is formed as an oscillating saw and controlled by the computer 7. A sorting system 13 follows the output of the optimizing saw 12. It is also controlled by the computer 7 which sorts the sawn products.

Figure 2:
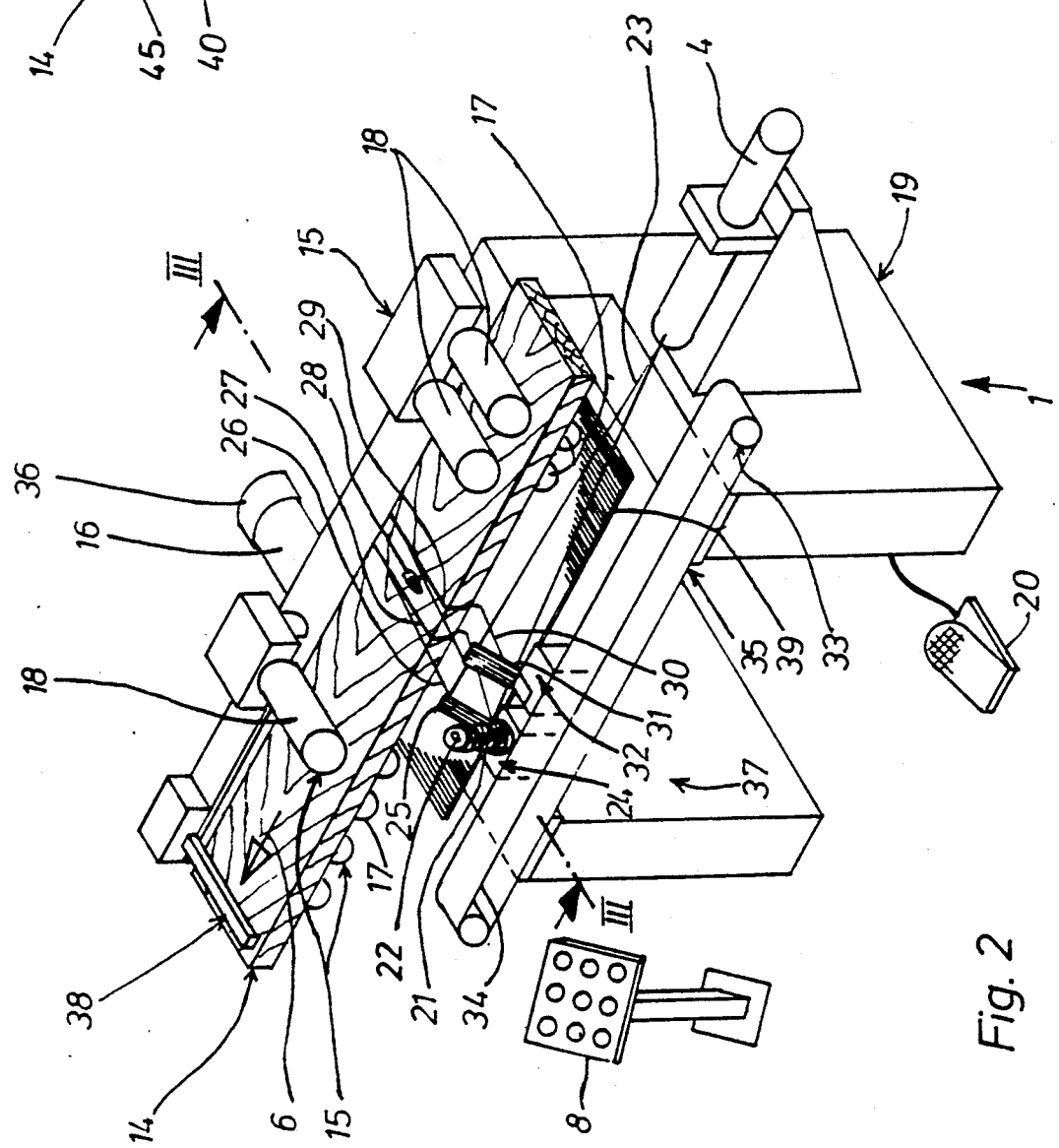
FIG. 2 is a schematic perspective view of the marking station in accordance with the present invention of FIG. 1.

As shown in FIG. 2, a piece of timber 14 is transported by a transporting device 15 through the marking station 1 in the movement direction 6. The transporting device 15 has lower rollers 17 which are driven by a drive 16 with not shown toothed belts, and upper rollers 18 which are arranged in alignment with the lower rollers 17 in a vertical direction. The upper rollers 18 are movable in a vertical direction to adjust to different thickness of the timber and are supported in a freely rotatable manner. The details of this device will be described in detail in another embodiment in connection with FIGS. 4–11. The transporting device 15 is supported on a frame 19 of the marking station 1, and the laser 4 is stationarily mounted on the same.

A foot switch 20 is provided for the operator. Its actuation can control the transporting speed of the transporting device 15. For example, by actuation of the foot switch a differently controlled transporting speed can be superposed by a basic transporting speed of a constant value.

The different control of the transporting speed is performed by a hand switch 21. When the operator turns the hand switch 21 in the direction of the timber 14, the transporting speed increases to a maximum at the abutment of the hand switch 21. When the hand switch 21 is turned opposite to the rear by the operator, the transporting speed reduces down to zero. The above mentioned key 22 is located on top of the hand switch 21. By pressing the key 22 the positions of the quality limits or separating planes on the piece of timber 14 indicated by the laser beam 23 are introduced into the computer 7 shown in FIG. 1.

The hand switch 21 is supported on a carriage 24. The carriage 24 is movable by the operator by hand parallel to the movement direction 6 by a guiding device which is not shown in FIG. 2. A first mirror 25 is mounted on the carriage 24. It deviates a part of the laser beam 23 perpendicularly to the movement direction 6 toward the piece of timber 14 and forms a laser fan 26. A first separating plane 27 in the movement direction 6 before a location of defect 28 is indicated on the timber 14 by the laser fan 26. The defect location 28 can be a knot, a crack, a resinous wood axudation, etc. The defect location 28 must be removed from the piece of timer 14. For this purpose a saw cut is made along the first separating plane 27 in the optimizing saw 12 later. A second such saw cut is performed along a second separating plane 29 which is also indicated in the marking station 1 and introduced by actuation of the key 22 with its position data into the computer 7 shown in FIG. 1.

In the embodiment of FIG. 2, the second separating plane 29 is indicated by a further laser fan 30 on the piece of timer 14. The laser fan 30 is produced by reflection on a partially permeable second mirror 31 which is mounted on a further carriage 32. The carriage 32 is also movable parallel to the movement direction 6 and along the guiding device. The further carriage 32 is driven by its own drive which is not shown in the drawings. The drive is activated by reciprocal activation of the hand switch 21 in a plane which is parallel to the movement direction 6. In this manner, the further carriage 32 can be moved in a motor-driven manner toward and away from the carriage 24 when desired. Correspondingly, the distance between the separating planes 27 and 29 can be changed, so that differently long extensions of the defect location 28 parallel to the movement direction 6 can be considered and indicated. When the separation planes 27 and 29 are positioned in an optimal manner relative to the defect location 28, the operator presses the key 22 and thereby simultaneously the position data of both separating planes 27 and 29 are introduced into the computer 7.

Since the second mirror 31 is partially permeable, a part of the laser beam 23 can pass to the first mirror 25. An action of the laser beam 23 on both mirrors 25 and 31 can also be performed in a different known manner.

If instead of the defect location 28 a quality limit is to be indicated on the timber 14, this is performed with only one of the mirrors 25, 31 and corresponding actuation of the key 22 for introducing the position data into the computer 7.

The carriage 24 and thereby the first mirror 25 are coupled with a first displacement transmitter 33 which is formed as a rotation transmitter. The coupling is performed by mounting the carriage 24 on a strand 34 of a toothed belt 35 which rotatably drives the first displacement transmitter 33 when the carriage 24 is moved along the guiding device.

On the other hand, the transporting device 15 is coupled through its drive 16 with a second displacement transmitter 36 which is also formed as a rotation transmitter. The second transmitter 36 produces second output signals corresponding to the position of the timber 14 along the transporting device 15. These second output signals as well as first output signals produced by the first displacement transmitter 33 are introduced in a known manner into the computer 7 shown in FIG. 1.

The indication of the quality limits or separating planes 27, 29 is performed in an indicating station part 37 of the marking station 1. In the embodiment of FIG. 2 the indication station part 37 is followed by a marking device 38 which is formed as an ink vapor printer. With the marking device 38 the quality limits and the separating planes 27, 29 indicated in the indicating station part 37 can be remainingly marked on the timber 14.

An inspection mirror 39 is mounted under the power rollers 17 of the transporting device 15 over a considerable part of the length of the marking station 1. With the help of the inspection mirror 39 the operator can observe a lower surface 40 of the timber 14 as to the quality limits and defect location 28 as shown in FIG. 3.

Figure 3:
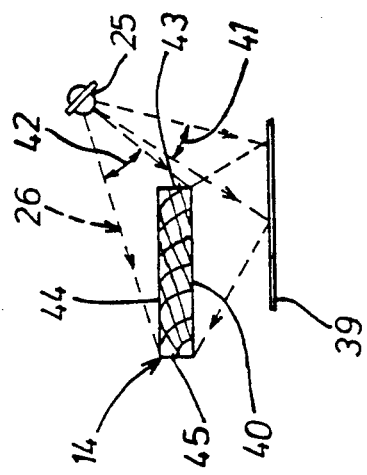
FIG. 3 is a part of a section taken along the line III—III in FIG. 2.

As can be seen from FIG. 3 the inspection mirror 39 also serves for reflecting a second part 41 of the respective laser fans 26 and 30 toward the lower surface 40 of the timber 14. It also serves for indicating the quality limits and the separating planes 27 and 29 on the lower surface. These indications on the lower surface 40 are observed by the operator via the inspection mirror 39.

FIG. 3 further shows that a first part 42 of the laser fan 26 falls directly on a first side surface 43 of the timber 14 which faces toward to first mirror 25 and also on an upper surface 44 of the timber 14, and indicates there the associated quality limits or separating planes 27 and 29 of FIG. 2.

During these steps a second side surface 45 of the timber 14, which faces away of the operator is not indicated with the laser fan 26 for preventing return reflection of the laser beams toward the operator. Still the second side surface 45 when needed can be observed by the operator as to the quality limits and defect locations. This is performed via an auxiliary mirror which will be described in connection with a further embodiment.

In all embodiments the like parts are identified with the same reference numerals.

The further embodiment is shown in FIGS. 4-11. In this embodiment only the first carriage 24 with the first mirror 25 are used, while the second carriage 32 with the second mirror 31 of FIG. 2 are not used. Due to the stationary arrangement of the laser 4, the carriage 24 is released from all needless masses and can be easily and fast displaced by the operator, so that in the running timber 14 in FIG. 2 the separating plates 27 and 29 are indicated shortly one after the other without difficulties and by pressing the key 22 can be introduced with their position data into the computer 7 of FIG. 1.

Figure 4:
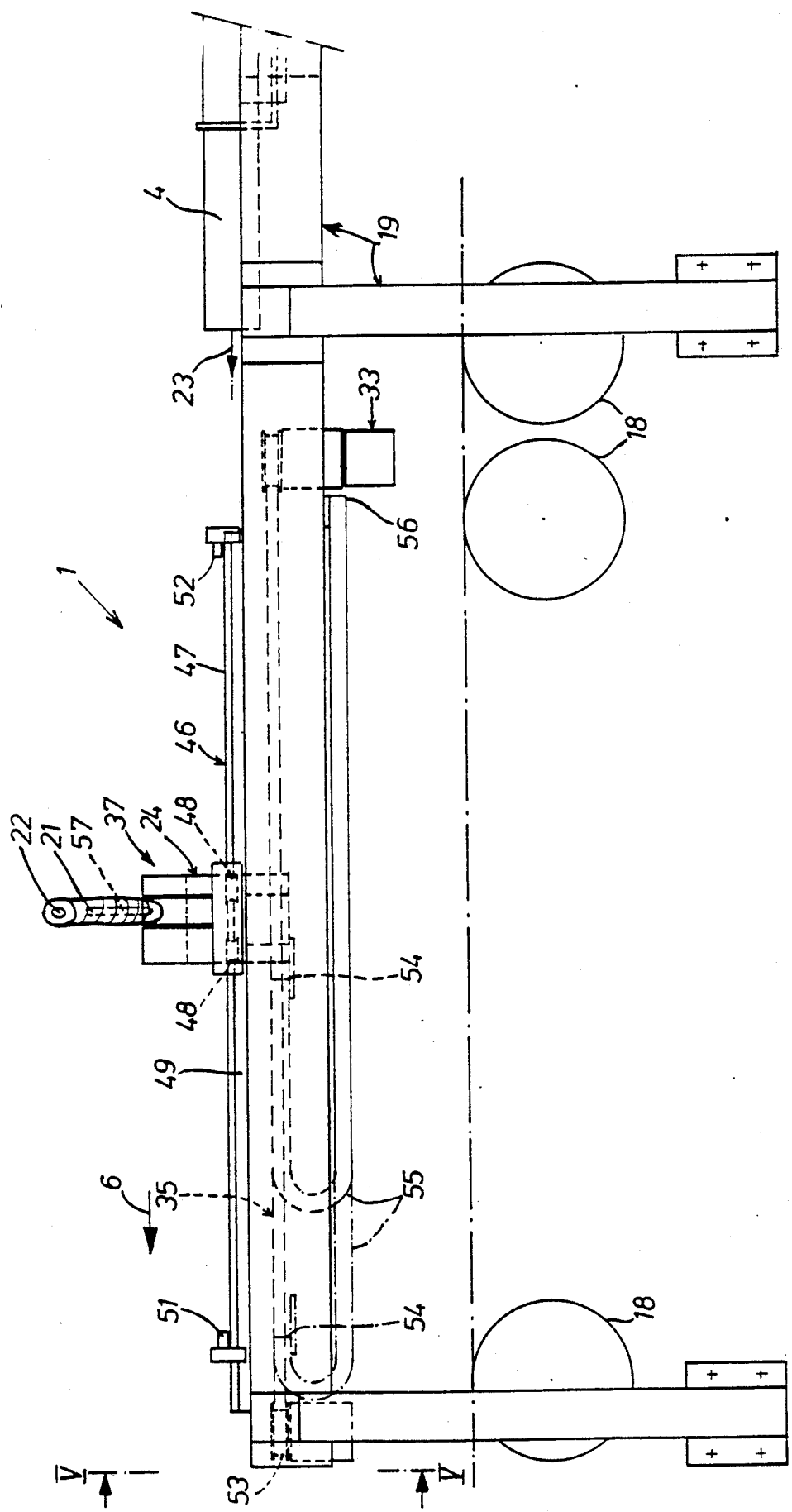
FIG. 4 is a side view of another embodiment of the invention with a mirror which is movable in the transporting direction of the timber, as seen by an operator.

In FIG. 4 the toothed belt 35 and the first displacement transmitter 33 are turned relative to FIG. 2 by −90° about a horizontal axis. FIG. 4 shows parts of a guiding device 46 for the carriage 24 especially one of two guiding rods 47 (FIG. 5) on which respectively running rollers 48 of the carriage 24 roll. The guiding rods 47 are mounted on a throughgoing supporting rail 49 which is fixed in FIG. 5 with screws 50 on the frame 19. The supporting rail 49 is provided on its ends with adjustable abutments 51 and 52 for displacement limiting of the carriage 24.

The toothed belt 35 is guided over a deviating roller 53 on its end which is located away from the first displacement transmitter 33.

One end 54 of flexible conductor arrangement 55 is mounted on the carriage 24. Its other end 56 is fixed in the vicinity of the first displacement transmitter 33 on the frame 19. Through the flexible conductor arrangement 55 all electrical functions of the carriage 24 are connected with the computer 7 of FIG. 1.

The hand switch 21 is removably mounted on a holder 57 of the carriage 24.

Figure 5:
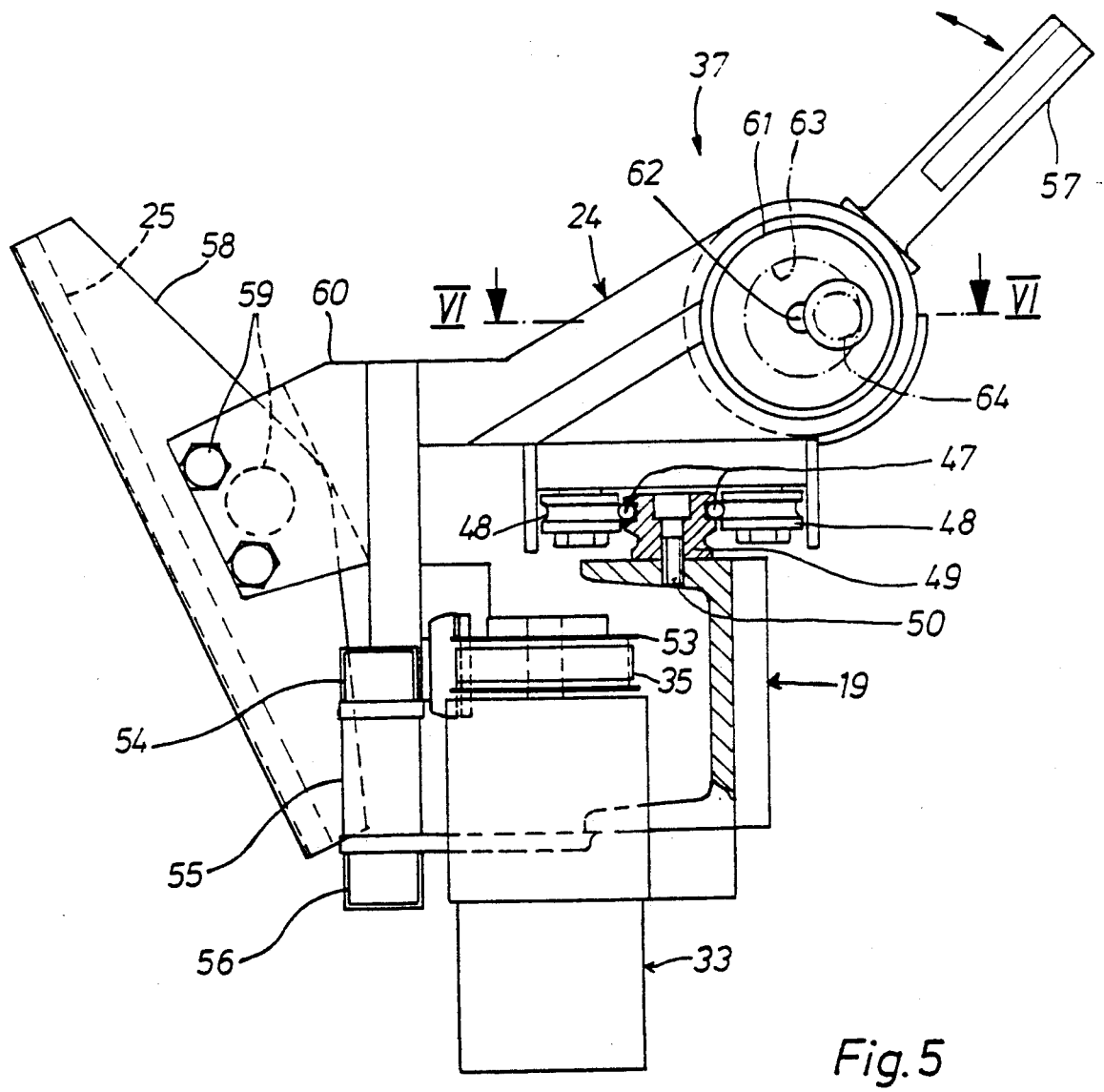
FIG. 5 is an end view of the marking station in accordance with line V—V in FIG. 4, on an enlarged scale.

The small rectangular shape of the flat first mirror 25 can be seen in FIG. 5. The first mirror 25 rests on frame 58 which is adjustably mounted on a lateral projection 60 of the carriage 24 by screw 59.

The holder 57 for the hand switch 21 which is not shown in FIG. 5 is screwed in a toothed ring 61 radially from outside. It is supported in the carriage 24 turnably about an axis 62 which is parallel to the movement direction 6 of FIG. 4. The toothed ring 61 has an inner toothing 63 which engages with a pinion 64 rotatably supported on the carriage 24. Therefore the turning movements of the holder 57 are converted into corresponding rotary movements of the pinion 64.

Figure 6:
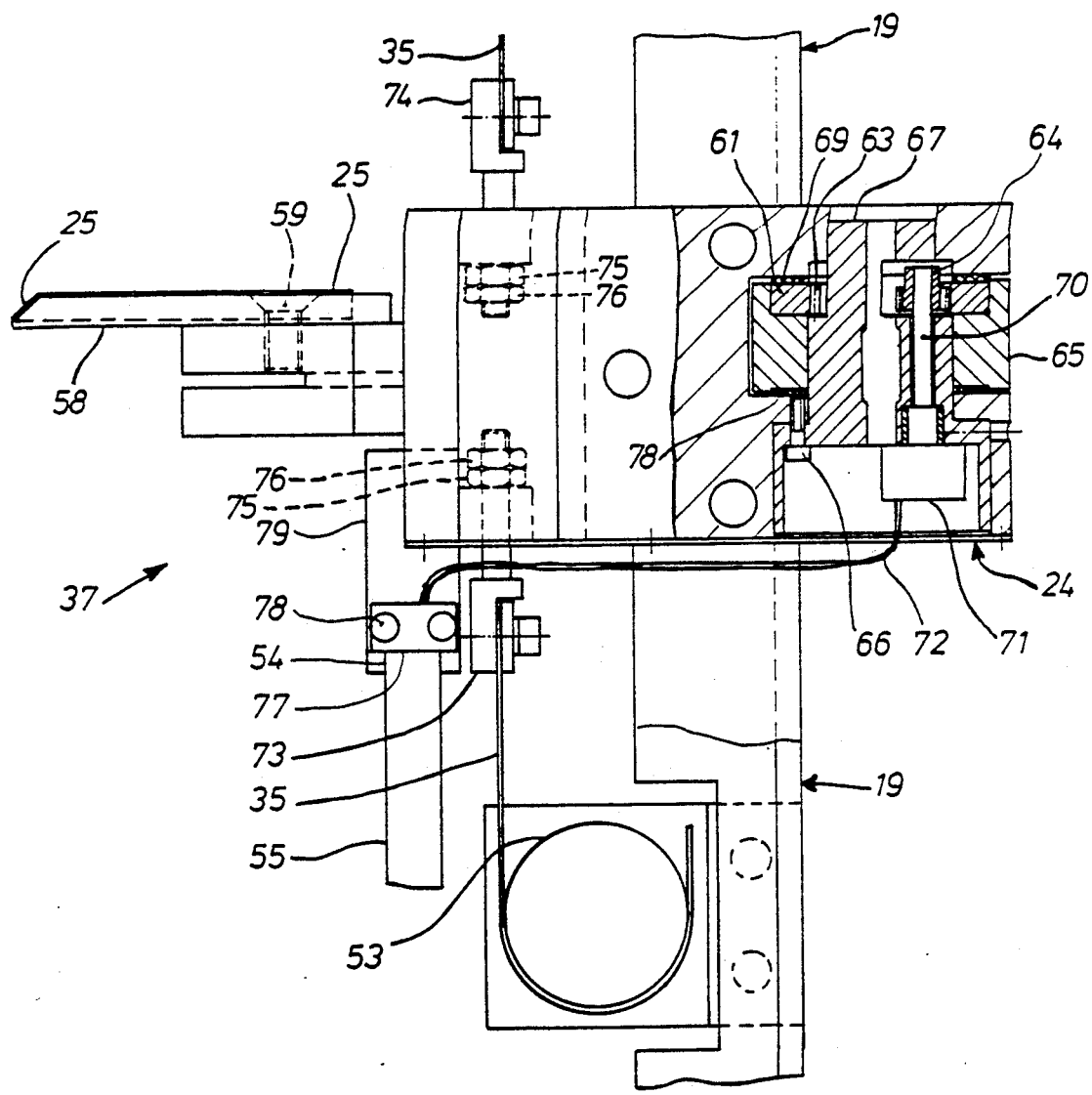
FIG. 6 is a view showing a section taken along the line VI—VI in FIG. 5.

FIG. 6 shows a ring 65 which is turnable on an axis 67 fixed on the carriage 24 by the screw 66. The holder 57 of FIG. 5 is screwed in the ring 65. The toothed ring 61 is also fixed on the ring 65. Sealing disc 68 and 69 are provided between the ring 65 and toothed ring 61 on the one hand, and the carriage 24 on the other hand. The pinion 64 is mounted on a shaft 70 which is rotatably supported in the axle 67 and coupled with the movable element of a potentiometer 71. The stationary part of the potentiometer 71 is fixed for example by glueing on the axle 67. An output conductor 72 of the potentiometer 71 is a component of the flexible conductor arrangement 55 of the FIG. 4.

As shown in FIG. 6, the toothed belt 35 is subdivided and fixedly screwed with a respective end on a coupling piece 73 and 74. Each coupling piece 73 and 74 extends with its free threaded end into the carriage 24 and is there adjustable with a nut 75 in its axial direction and fixable with a counter nut 76. In this manner the mounting position of the toothed belt 35 relative to the carriage 24 is adjusted on the one hand, and the tension of the toothed belt 35 is adjusted on the other hand.

FIG. 6 also shows how the end 54 of the flexible conductor arrangement 55 is fixed by a clamp 77 with screws 78 on a connection piece 79 of the carriage 24. For maintaining the visibility, no further electrical conductors of the flexible conductor arrangement 55 are indicated in addition to the output conductors 72.

Figure 7:
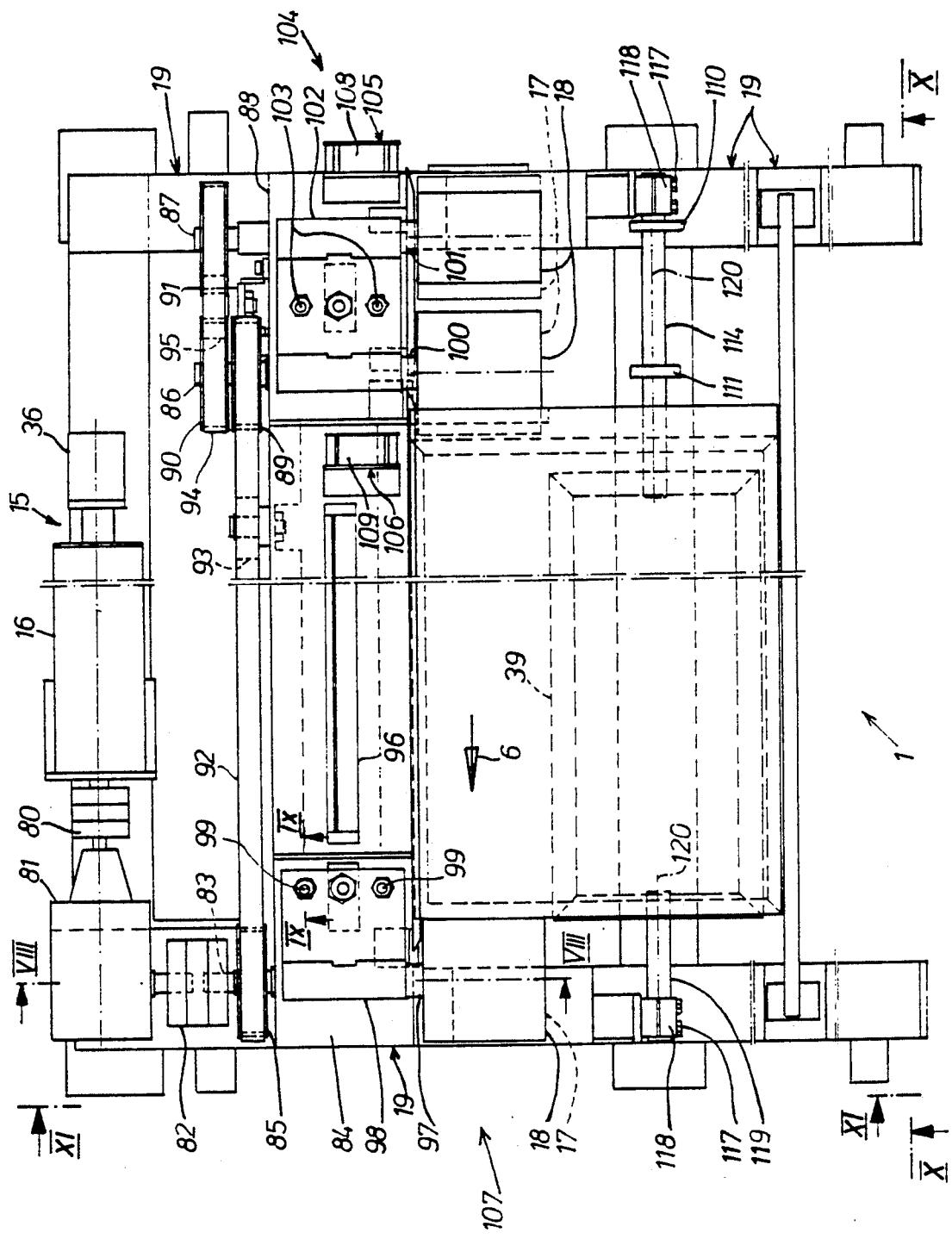
FIG. 7 is a plan view of the marking station in accordance with the present invention according to FIG. 4.

FIG. 7 shows the details of the transporting device 15. The drive 16 is mounted on the frame 19 and drives on the one hand the second displacement transmitter 36 and on the other hand a shaft 83 through an elastic coupling 80, an angular transmission 81 and a further elastic coupling 82. The shaft 83 is rotatably supported in a bearing block 84 of the frame 19. A belt pulley 85 and the frontmost lower roller 17 as considered in the movement direction 6 are mounted on the shaft 83. The central and the rearmost of the lower rollers 17 are mounted respectively on a shaft 86 and 87 which are supported in a further bearing block 88 of the frame 19. Belt pulleys 89 and 90 are also mounted on the shaft 86, while a belt pulley 91 which is in alignment with the belt pulley 90 is mounted on the shaft 87. An endless toothed rim 92 runs over the belt pulleys 85 and 89 and is tensioned by an adjustable tensioning roller 93. An endless toothed rim 94 is guided over the belt pulleys 90 and 91 and is tensioned by an adjustable tensioning roller 95. In this manner all three lower rollers 17 are driven with the same rotary direction and the same peripheral speed. The transporting speeds obtained in this manner for the timber 14 can be changed in the above described manner when needed.

The auxiliary mirror 96 which is mentioned in connection with FIG. 3 is also shown in FIG. 7. With this mirror the operator can observe the second side surface 45 (FIG. 3) of the timber 14 as to the quality limits and defect locations. The auxiliary mirror 96 is adjustable as to its inclination about an axis extending parallel to the movement direction 6. The upper rollers 18 are arranged perpendicularly above the lower roller 17 which are not shown in FIG. 7. The frontmost roller 18 is supported in a freely rotatable manner about an axle 97 which is mounted on a cantilever 98 by two rods 99 movable in a vertical direction. Similarly the central and rearmost upper rollers 18 are freely rotatably mounted about an axle 100 and 101 which are mounted on a head piece 102 by two rods 103 movable in a vertical direction.

A first light barrier 105 and a second light barrier 106 are arranged parallel to the longitudinal axes of the rollers 17 and 18 in an inlet region 104 of the marking station 1. In an outlet region 107 of the marking station 1 such light barriers are not needed. Receiver 108 and 109 of the light barriers 105 and 106 are mounted near the bearing block 88, while holding arms 110 and 111 for transmitters 112 and 113 (FIG. 10) of the light barriers 105 and 106 are mounted on a shaft trunion 114 of the inspection mirror 39 in an adjustable fashion.

Figure 10:
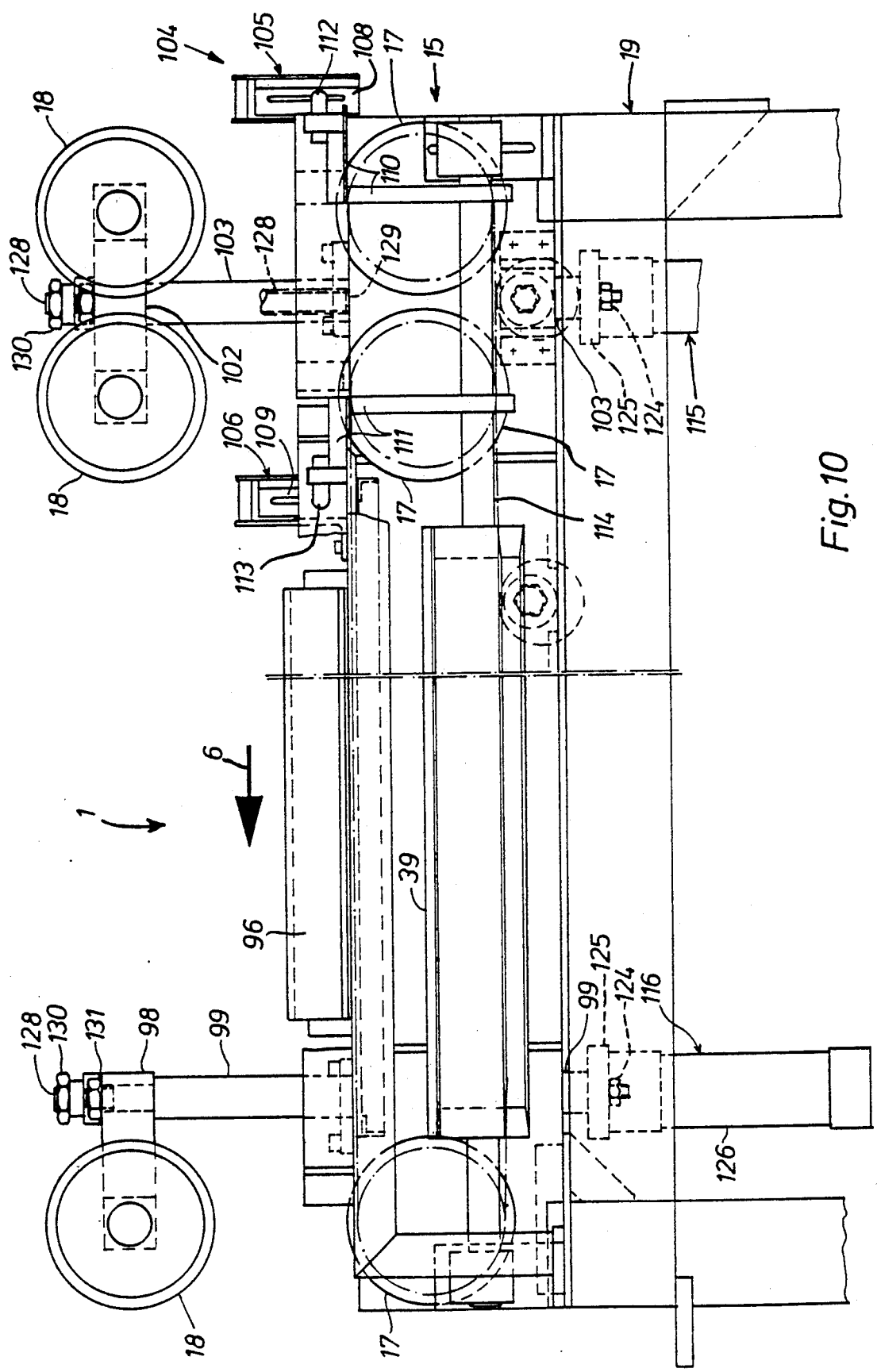
FIG. 10 is a side view of the marking station according to line X—X in FIG. 7, as seen by the operator.

By a timber 14 which runs in the movement direction 6 into the inlet region 104, the first light barriers 105 is darkened. Thereby a pneumatic cylinder-piston unit 115 shown in FIG. 10 is actuated and the rod 103 with its both upper rollers 18 is pulled downwardly. Thereby the timber which ran into the inlet region 104 is acted upon the upper rollers 18 with a pressure from above and pressed into driving contact with the lower rollers 17. In this manner a slippage-free driving of the timber by the transporting device 15 in the marking station 1 is guaranteed.

Immediately upon leaving the central roller pair 17, 18, the leading portion of the timber 14 makes dark the second light barrier 106 and activates in a known manner the electrical transmission paths between the marking station 1 and the computer 7 of FIG. 1. Through the end of the timber the light releases one after the other in the light barriers 105 and 106.

An additional light barrier is not required in the outlet region 107 for actuating the frontmost upper roller 18 located there, since this actuation is performed by a known control circuit with pulses corresponding to the path covered from the beginning of the timber in the marking station 1. Simultaneously for hitting of the beginning of the timber, the rods 99 with the associated upper roller 18 are pulled downwardly by actuation of a pneumatic cylinder-piston unit 116 of FIGS. 9 and 10.

The shaft end 114 is held adjustably in its rotary position by a bearing block clampable with screws 117. On the opposite side of the inspection mirror 39, a similar shaft end 119 is mounted in an axial alignment with the shaft end 114 and held clampingly in the same manner. Thereby the inspection mirror 39 can be adjusted to each desired turning position about a longitudinal axis 120 parallel to the movement direction 6.

Figure 8:
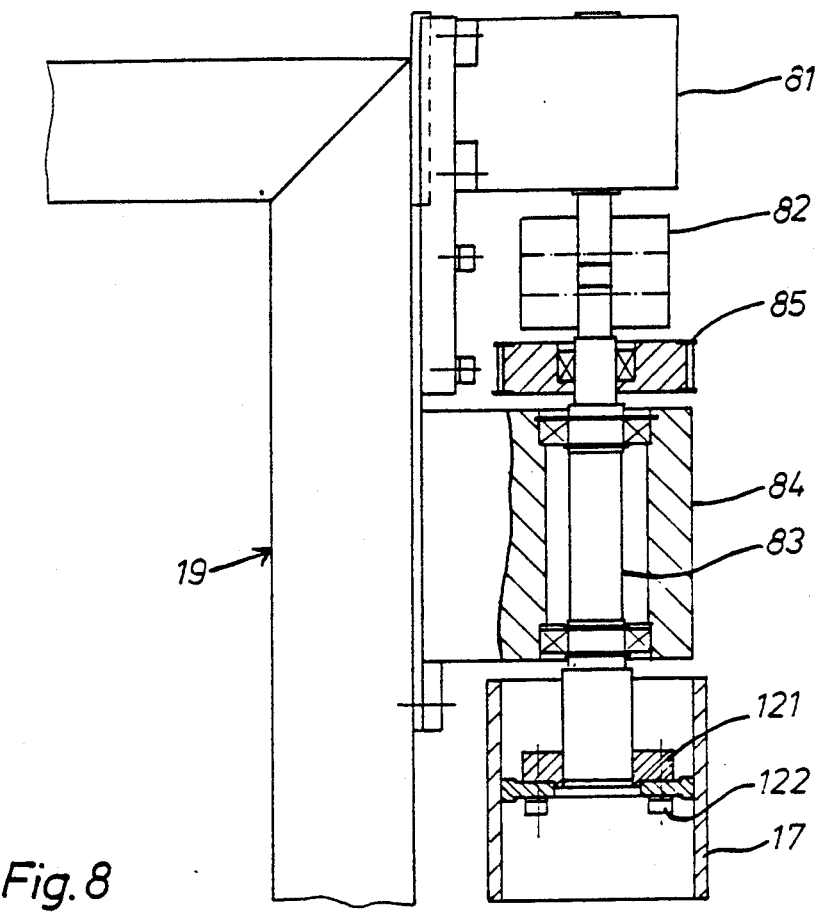
FIG. 8 is a view showing a section taken along the line VIII—VIII in FIG. 7.

FIG. 8 shows the details of the construction and support of the shaft 83. A flange 121 is welded on the lower end of the shaft 83 as shown in FIG. 8. The lower roller 17 is screwed on the flange 121 with screws 122.

Figure 9:
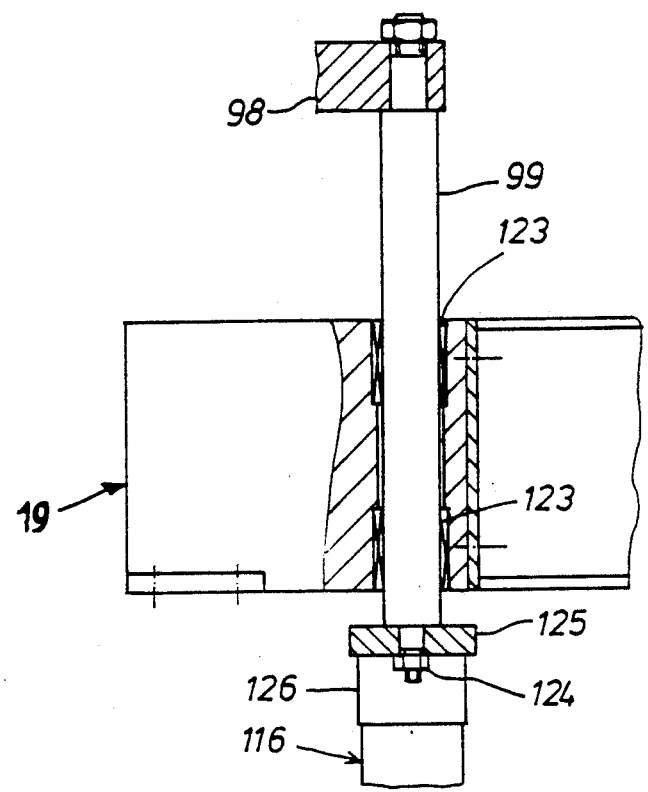
FIG. 9 is a view showing a section taken along the line IX—IX in FIG. 7.

FIG. 9 shows the mounting of the cantilever 98 on one of two mutually parallel rods 99, and the support of the rod 99 through ball bearings 123 in the frame 19. As can be seen from FIG. 11, each of the both rods 99 is screwed downwardly by a nut 124 with a yoke plate 125. A cylinder 126 of the pneumatic cylinder-piston 116 is mounted between the nuts 124 also on the yoke plate 125. A piston rod 127 of the pneumatic cylinder-piston 116 is screwed with the frame 19. The actuation of the pneumatic cylinder-piston unit 116 moves the cylinder 126 with both rods 19 up and down, while the piston rod 127 remains stationary.

FIG. 10 shows the upper rollers 18 which are lifted by the pneumatic cylinder-piston unit 115, 116 to their uppermost end position. Thereby a maximum distance between the oppositely located roller pairs 17 and 18 is produced. Since the timber has a height which on the one hand is smaller than this maximum roller distance and on the other hand varies, a stroke limit is provided both for the head piece 102 and for the cantilever 98. For this purpose, a threaded pin 128 is provided each respectively between the rods 99 and between the rods 103. It is screwed with its lower end 129 with the frame 19. The threaded pins 128 extend upwardly with the lateral play through openings of the cantilever 98 and head piece 102 and carry above the same an adjusting nut 130. A felt ring 131 is glued on the lower side of the adjusting nut 130. The felt ring 131 acts as a damper when the pneumatic cylinder-piston units 115, 116 move the head piece 102 or the cantilever 98 upwardly. By adjusting the adjusting nut 130, the stroke of the upper rollers 18 can be adjusted to the respective thickness of the timber in an optimal manner.

Figure 11:
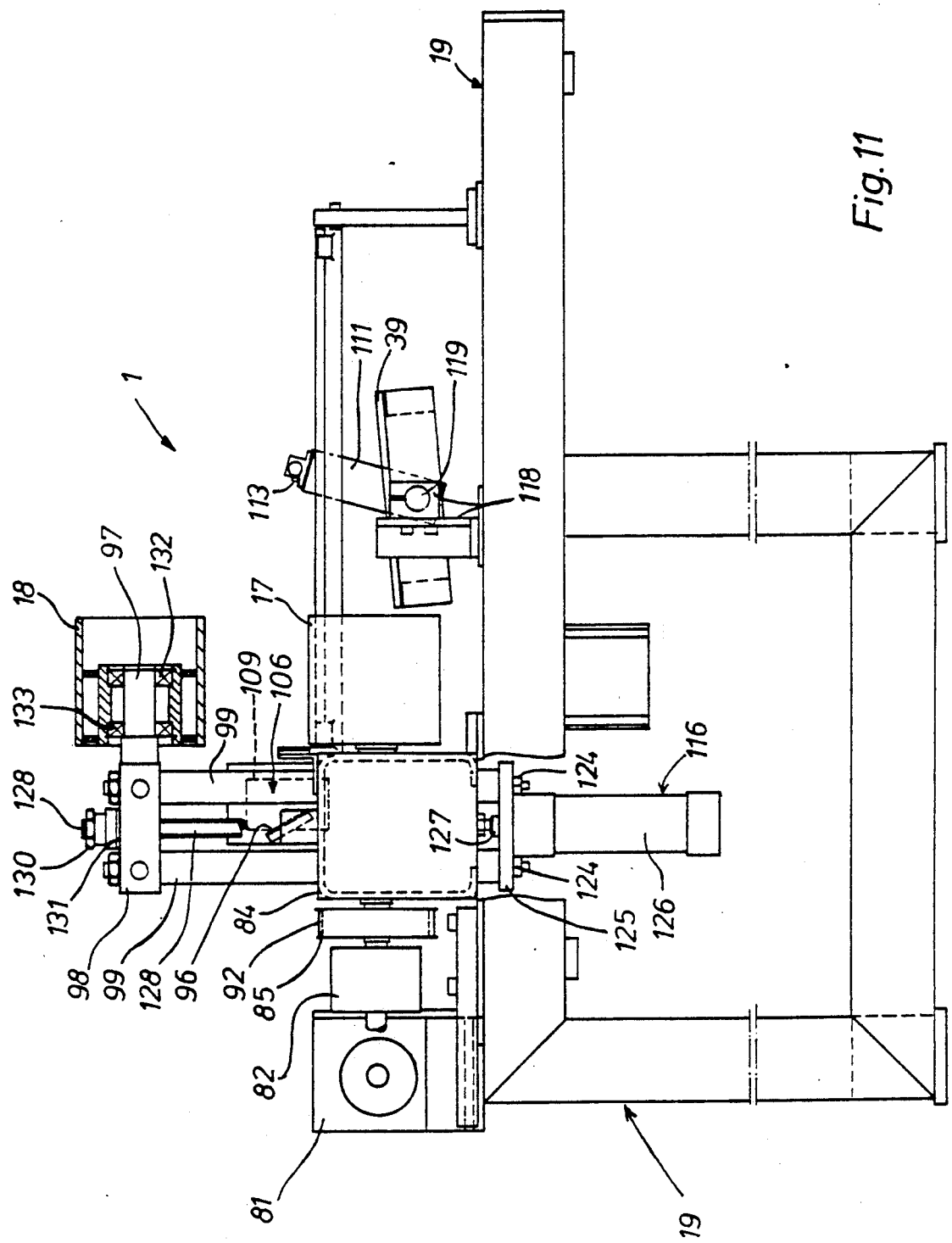
FIG. 11 is an end view according to line XI—XI in FIG. 7.

FIG. 11 shows further details of the marking station 1. The upper roller 18 is rotatably mounted on the axle 97 of the cantilever 98 through roller bearings 132 and 133 in a freely-rotatable manner.

Figure 12:
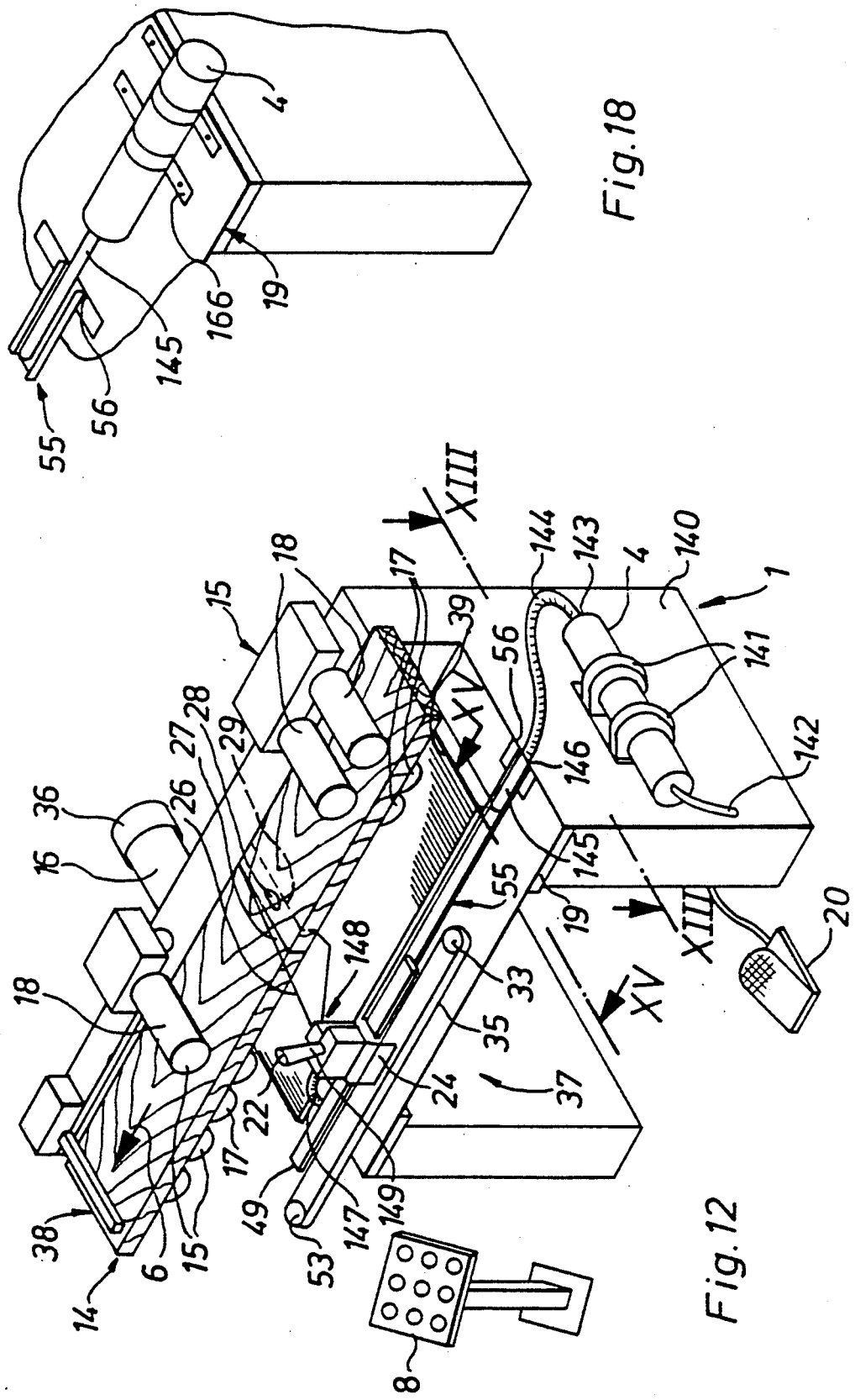
FIG. 12 is a schematic perspective view similar to that of FIG. 2 of another embodiment of the marking station according to the present invention.

In the embodiment of FIG. 12, the laser 4 is stationarily secured to the side wall 140 of the frame 19 with a mounting 141. The laser 4 is provided with a feed cable 142 and an optical outlet 143. A connection part 144 of a flexible optical waveguide 145 is connected with the optical outlet 143. The optical waveguide 145 can, for example, be made of a glass fiber cable. The other end of the connection part 144 is merged into a stationary second end 146 of the optical waveguide 145. A portion of the optical waveguide 145 is arranged in a plane extending parallel to the transporting (movement) direction 6 whereby the first end 145 of the optical waveguide 147 is connected with an optical transmitter 148. The foregoing portion of the optical waveguide 145 is supported in, per se known, flexible conductor arrangement 55 formed as a power circuit. The light (optical) transmitter 148 is supported on the carriage 24 and is provided with a handle 149 with which the optical transmitter 148 and the carriage 24 are displaceable together along the supporting rail 49. The key 22 is formed integrally with the handle 149 and is easily actuatable by the operator.

Figure 13:
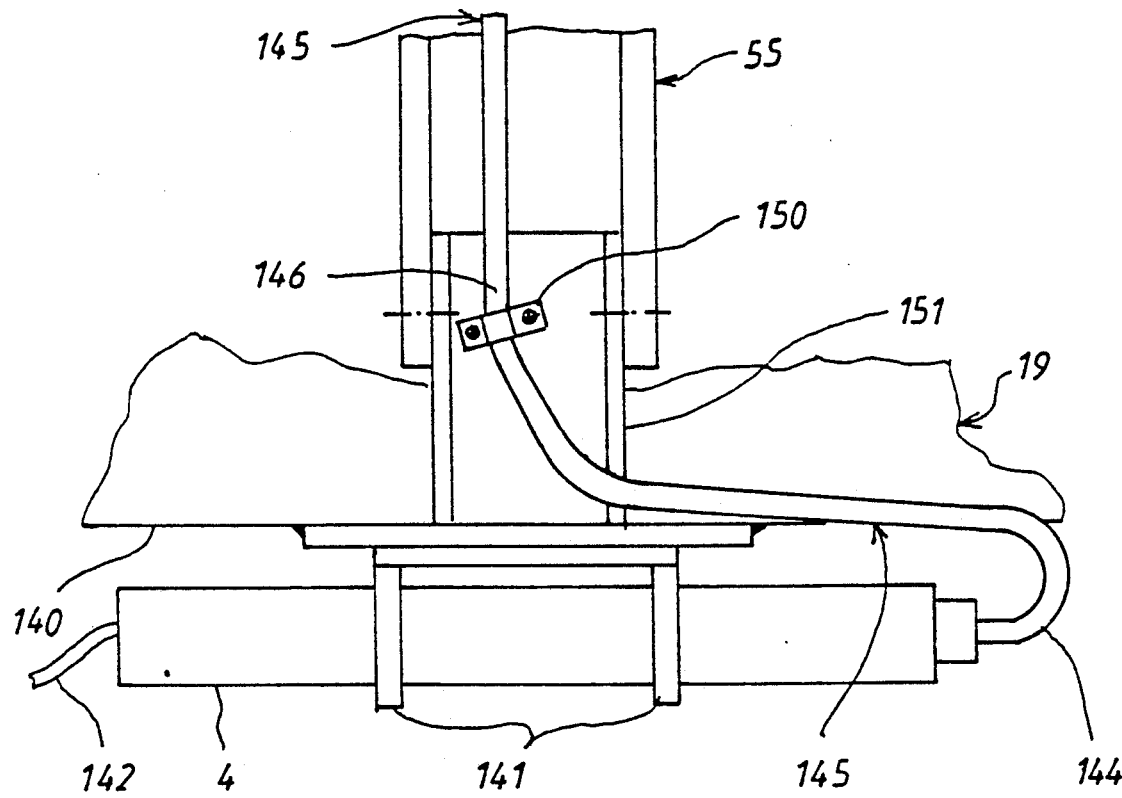
FIG. 13 is a partial cross-sectional view taken along the line XIII—XIII in FIG. 12.

FIG. 13 shows a transition from the connection part 144 of the optical waveguide 145 in the stationary end 146 of the latter. At the second end 146, the optical waveguide 145 is connected by a clip 150 with a stationary end section 151 of the flexible conductor arrangement 55. The section 151 is fixed on the frame 19.

Figure 14:
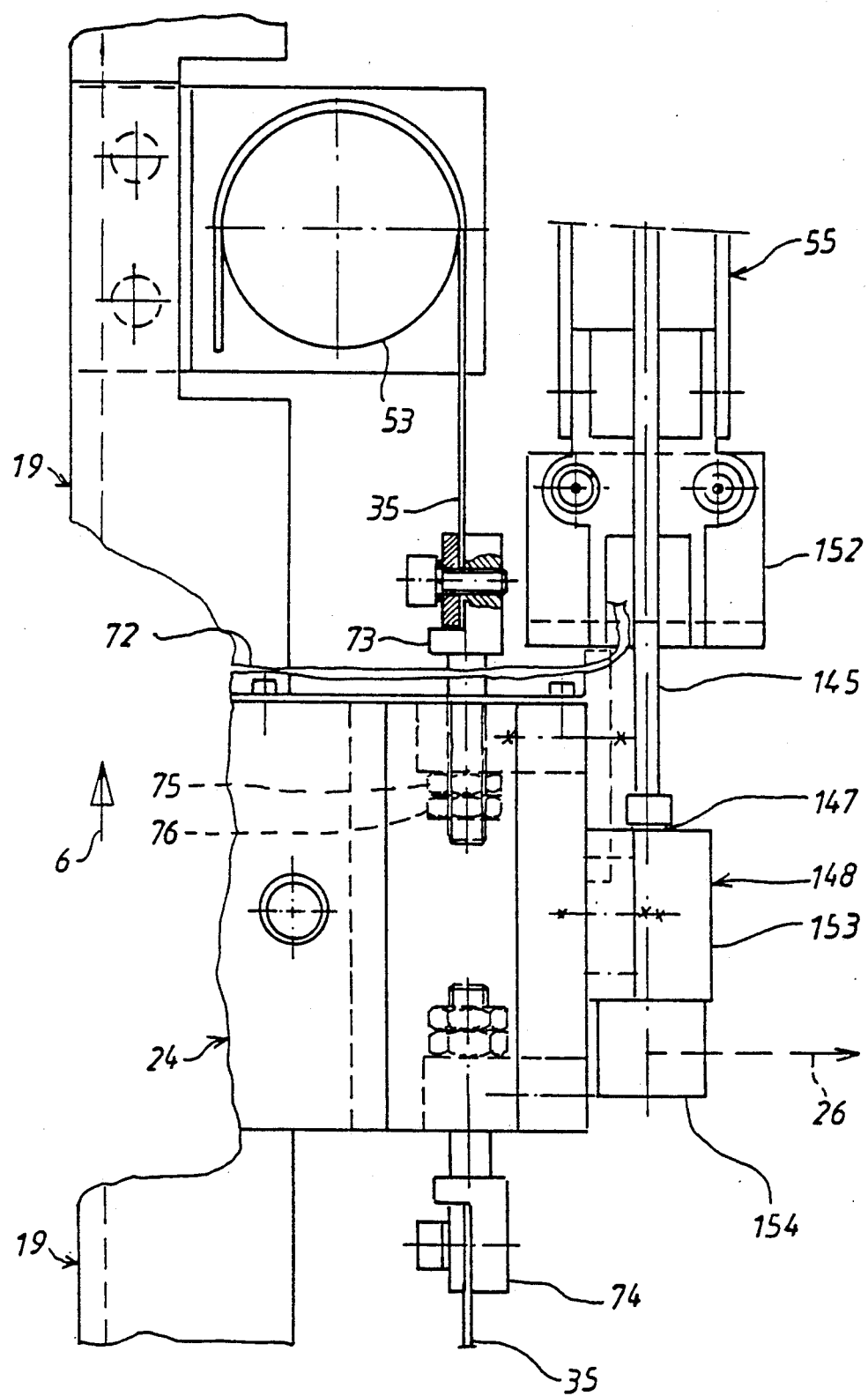
FIG. 14 is a schematic partial plan view of a marking station shown in FIG. 12.
Figure 15:
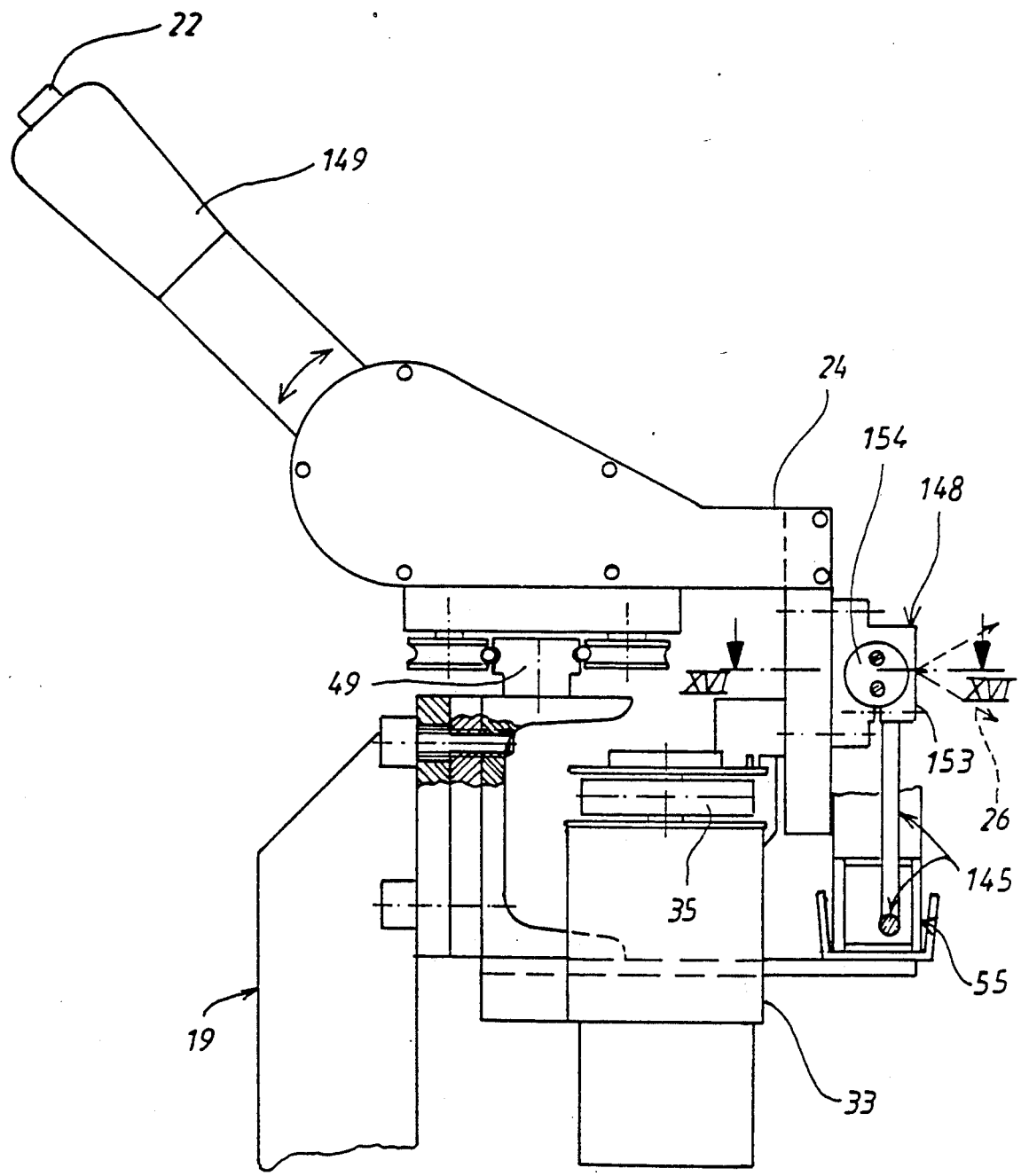
FIG. 15 is a cross-sectional view taken along the line XV—XV in FIG. 12.

FIG. 14 shows another end section 152 at the other end of the conductor arrangement 55 which is secured to the carriage 24. The first end 147 of the optical guide 145 extends into a coupling 153 of the optical transmitter 148. On the side portion of the coupling 153, which is opposite to that associated with the waveguide 145, there is arranged a routing housing 154 of the optical transmitter 148 out of which the laser fan 26 is directed as shown by a dash arrow in a plane perpendicular to the transporting direction 6. FIG. 15 shows in more details arrangement of parts shown only relatively schematically in FIG. 12.

As shown by a double arrow in FIG. 15, the handle 149 is movable in opposite direction for changing the transporting speed of the timber 14 in the transporting direction 6.

Figure 16:
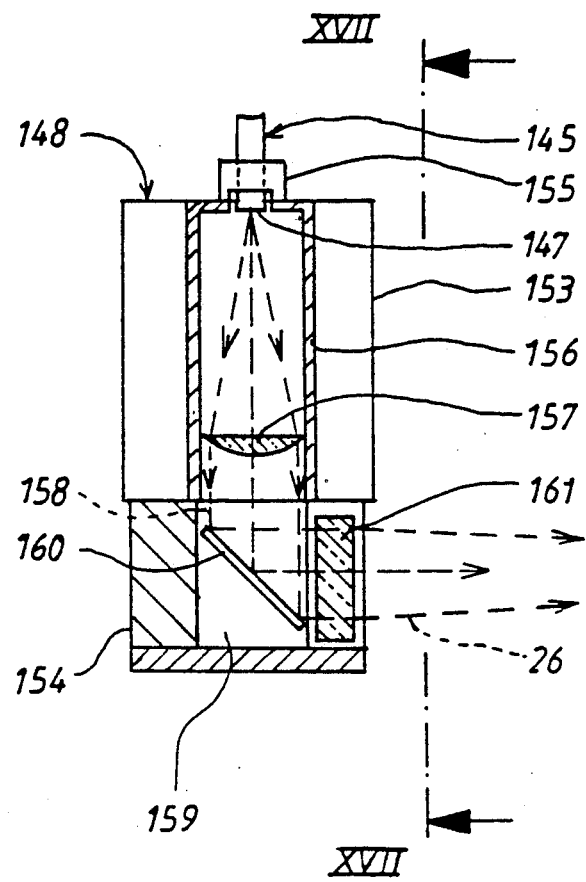
FIG. 16 is a partial enlarged cross-sectional view taken along the line XVI—XVI in FIG. 15.

As shown in FIG. 16, the waveguide 145 is secured to the coupling 153 with a cap screw 155. The first end 147 of the waveguide 145 projects into a tubular part 156 of the coupling 153. The first end 147 of the waveguide 145 irradiates a dash light cone onto a collimator lens 157 that transforms the light cone into a beam 158 of rays parallel to its optical axis. The beam 158 enters a chamber 159 of the routing housing 154 and falls onto a deviating mirror 160 wherefrom the rays are directed to a cylindrical lens 161 transverse thereto. The laser fan 26 projects from the lens 161.

Figure 17:
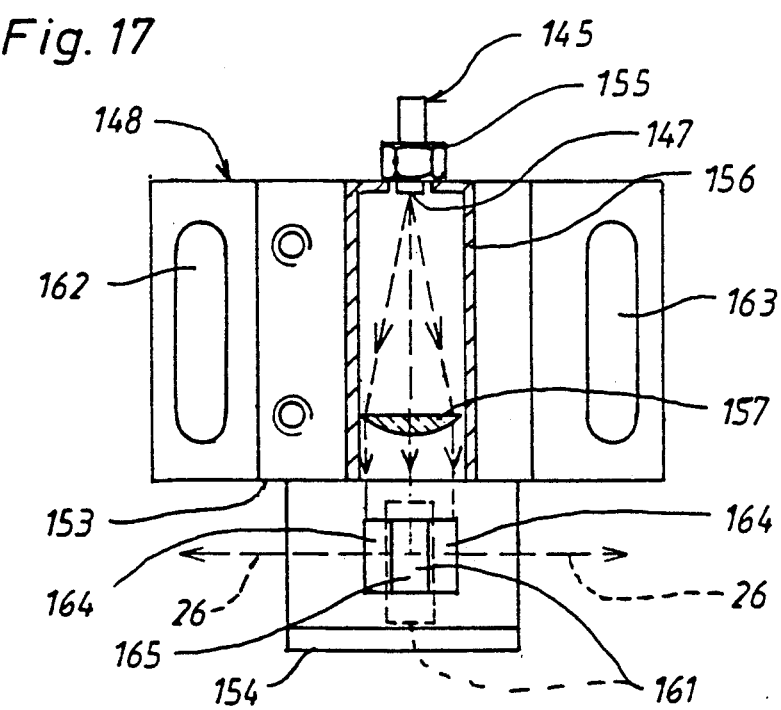
FIG. 17 is a partial cross-sectional view taken along the line XVII—XVII in FIG. 16.

As shown in FIG. 17, the optical transmitter 148 is adjustable relative to the carriage 24 by means of longitudinal openings 162 and 163. The routing housing 154 is provided with a recess 164 that defines a central window 165 for light exit. In this embodiment, the laser fan 26 when leaving the lens 161, still has a certain width but converges until it impinges on the timber 14, to such an extent that the separating plane 27 or 29 or the quality limits can be indicated with a sufficiently narrow laser beam.

In FIG. 18, the laser 4 is fixed to the, frame 19 by supports 166 in such a manner that the longitudinal axis of the laser 4 is coaxial with the longitudinal axis of the waveguide 145.

Such a mounting permits to do away with the connection part 144 of the waveguide 145.

It will be understood that each of the elements described above, or two or more together, may also find a useful application in other types of constructions differing from the types described above.

While the invention has been illustrated and described as embodied in a marking station for timber, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A marking station for defect locations and quality limits in timber, comprising a transporting device arranged to transport a timber in a movement direction through the marking station; a device for changing a transporting speed of the timber in the marking station; an indicating station part provided with a laser transmitting element comprising a light transmitter and operative for indicating on the timber with a laser beam a first separating plane in the movement direction before a defect location and a second separating plane in the movement direction behind the defect location as well as for indicating quality limits, said laser transmitting element being movable by an operator along guiding means parallel to the movement direction relative to the timber to indicating positions corresponding to the separating planes and the quality limits; a computer receiving the indicating positions of said laser transmitting element in the movement direction; a stationary laser connected to said light transmitter through a flexible optical waveguide; and said light transmitter transmitting a laser fan transversely to said movement direction, so that a first part of said laser fan directly impinges on a first side surface of the timber which faces toward said light transmitter and also on an upper surface of the timber to indicate thereon the associated separating plane and quality limit.

2. A marking station as defined in claim 1, wherein at least a portion of said optical waveguide is arranged in a plane extending parallel to said movement direction, said optical waveguide having a first end connected to said light transmitter and a second end arranged stationarily.

3. A marking station as defined in claim 2, wherein said optical waveguide includes a connection portion for connecting said laser with said second end.

4. A marking station as defined in claim 1, wherein said optical waveguide comprises a first end connected to said light transmitter; said light transmitter comprising a light outlet; an optical system being connected between said first end and said light outlet.

5. A marking station as defined in claim 1; and further comprising an optimizing saw arranged to cut the timber in an optimal manner and controlled by said computer.

6. A marking station as defined in claim 1; and further comprising a flat inspection mirror which is arranged stationarily under a path of the timber and extends in said movement direction, said inspection mirror being located so that a second part of said laser fan is reflected from said inspection mirror to a lower surface of the timber and indicates there the associated separating plane and quality limit.

7. A marking station as defined in claim 1; and further comprising a carriage guided by said guiding means, said lower transmitting element being mounted on said carriage.

8. A marking station as defined in claim 1; and further comprising an inlet region and an outlet region, said transporting speed of said transporting device being controllable in dependence upon a position of said laser transmitting element along said guiding means so that the transporting speed is maximal when said laser transmitting element is located in said inlet region and is minimal when said laser transmitting element is located in said outlet region.

9. A marking station as defined in claim 8; and further comprising means for selectively superposing onto the controllable transporting speed a basic transporting speed of a constant value.

10. A marking station as defined in claim 9, wherein said means for selectively superposing the basic transporting speed includes a foot switch actuatable by an operator.

11. A marking station as defined in claim 1; and further comprising a first displacement transmitter coupled with said laser transmitting element and producing first output signals corresponding to a position of said laser transmitting element along said guiding means, and a second displacement transmitter coupled with said transporting device and producing second output signals corresponding to a position of the timber along said transporting device, said computer receiving said first output signals and said second output signals.

12. A marking station as defined in claim 1; and further comprising a marking device located after said indicating station part and arranged to remainingly mark the separating planes and the quality limits indicated in said indicating station part, said marking device being controlled by said computer.

* * * * *

UNITED STATES PATENT AND TRADEMARK OFFICE
CERTIFICATE OF CORRECTION

PATENT NO. : 5,042,341

DATED : August 27, 1991

INVENTOR(S) : Ernst Greten, et. al.

It is certified that error appears in the above-identified patent and that said Letters Patent is hereby corrected as shown below:

On the Title page

Item [75] The place of residence of the inventor Klaus Jurisch should read --HATTSTEDTERMARSCH--

Item [73] The place of business of the assignee FAGUS-GRECON GRETEN GMBH

& CO KG should read -- Alfeld (Leine)--.

Signed and Sealed this

Twenty-sixth Day of January, 1993

Attest:

STEPHEN G. KUNIN

Attesting Officer     Acting Commissioner of Patents and Trademarks